United States Patent [19]

Murray et al.

[11] Patent Number: 4,514,383

[45] Date of Patent: Apr. 30, 1985

[54] SUNSCREEN COMPOSITIONS CONTAINING VINYLOGOUS AMIDES

[75] Inventors: William V. Murray, Belle Mead; Charles E. Clum, Kingston; Elvin R. Lukenbach, Somerset, all of N.J.

[73] Assignee: Johnson & Johnson Baby Products Company, New Brunswick, N.J.

[21] Appl. No.: 375,072

[22] Filed: May 5, 1982

[51] Int. Cl.³ .................... A61K 7/42; A61K 31/13
[52] U.S. Cl. .................... 424/59; 424/60; 424/64; 424/70; 514/567; 514/649; 514/658
[58] Field of Search .................... 424/59, 60, 64, 70, 424/168, 325, 330; 564/305, 342, 502

[56] References Cited

U.S. PATENT DOCUMENTS 4,178,449 12/1979 Dusza et al. .................... 544/281

FOREIGN PATENT DOCUMENTS 0009609 4/1980 European Pat. Off. .

OTHER PUBLICATIONS

CA: 80: 119,856, (1974).
Index Chemicus, vol. 27, #85940, (1967), and vol. 28, #90760, (1968).
Giese et al., J. of the American Pharmaceutical Assn. Scientific Ed., pp. 30–36, 1950.

*Primary Examiner*—Sidney Marantz
*Assistant Examiner*—Shawn P. Foley

[57] ABSTRACT

Novel sunscreen compositions comprising at least one vinylogous amide compound are described as well as methods of protecting the human skin from damaging radiation.

7 Claims, No Drawings

SUNSCREEN COMPOSITIONS CONTAINING VINYLOGOUS AMIDES

BACKGROUND OF THE INVENTION

This invention relates to new and useful ultraviolet radiation sunscreen agents and compositions and to methods of protecting the human skin against the potentially harmful effects of sunlight.

It is well documented that human skin is sensitive to sunlight containing radiation of wavelengths between about 290 nanometers (nm) and 400 nm as well as artificial light. Ultraviolet radiation of wavelengths between about 290 nm and 320 nm (UV-B region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years concern has also been expressed regarding ultraviolet radiation of wavelengths above 320 nm (UV-A region) and the adverse effects of such radiation on human skin.

In view of the above, protection from the erythemal effects of sunlight produced by ultraviolet radiation within the UV-B region has been the traditional objective of sunscreen agents and compositions and as a result most compounds utilized as sunscreen agents have had light absorbance maxima within this UV-B region. Recently, as a result of growing concern for damage to the skin in the UV-A region, compounds capable of absorbing ultraviolet radiation in this region of the spectrum are becoming increasingly desirable but are generally unavailable.

Currently, the most widely utilized commercial sunscreen agents include para-amino benzoic acid derivatives, oxybenzones, methoxycinnamates and salicylates.

A desirable sunscreen agent should have absorbance maxima in the range of between 290 nm and 350 nm; have a molar absorptivity of greater than 10,000; be non-toxic, colorless and odorless; be heat and light stable; be water-insoluble and be easily and relatively inexpensively produced. While the readily available commercial sunscreen agents have enjoyed a measure of success, they all lack one or more of the above desirable properties.

OBJECTS OF THE INVENTION

It is an object of the present invention to provide improved sunscreen agents and compositions.

It is another object of the present invention to provide sunscreen compositions containing sunscreen agents that overcome the disadvantages of heretofore available materials and provide adequate and safe protection for human skin.

It is a further object of this invention to provide methods of protecting human skin against the harmful effects of sunlight.

These and other objects and features of the present invention will become readily apparent to one skilled in the art from the detailed description given hereinafter.

SUMMARY OF THE INVENTION

The foregoing objects and other features and advantages of the present invention are achieved by sunscreen compositions containing one or more vinylogous amides as the sunscreen agent.

DETAILED DESCRIPTION OF THE INVENTION

The sunscreen compositions of the present invention contain as an active sunscreen agent at least one vinylogous amide compound selected from the group consisting of $$R_1-\overset{O}{\overset{\|}{C}}-\underset{R_2}{\overset{}{C}}=\underset{R_3}{\overset{}{C}}-\underset{}{\overset{R_5}{\overset{|}{N}}}-R_4 \text{ and } R_1-Y-\overset{O}{\overset{\|}{C}}-\underset{R_2}{\overset{}{C}}=\underset{R_3}{\overset{}{C}}-\underset{}{\overset{R_5}{\overset{|}{N}}}-R_4$$

wherein $R_1$ is selected from alkyl, cycloalkyl, alkenyl, cycloalkenyl, aryl, substituted aryl or alkaryl of from 1–18 carbon atoms which may be optionally interrupted or substituted by N or O. When N is present it may be as a primary, secondary or tertiary amine, quaternary ammonium salt or amide and when O is present it may be as an alcohol, carboxylic acid, ester or ether.

$R_2$ and $R_3$ may be the same or different and are selected from hydrogen, alkyl, alkenyl, cycloalkyl or cycloalkenyl of from 1–8 carbon atoms and may be optionally interrupted or substituted by N or O as defined above. $R_1$, $R_2$ and $R_3$ may also form carbocyclic or heterocyclic rings.

$R_4$ and $R_5$ may be the same or different and are selected from hydrogen, alkyl, alkenyl, aryl and substituted aryl, alkaryl, cycloalkyl or cycloalkenyl of from 1–18 carbon atoms and may be optionally interrupted or substituted by N or O as defined above. $R_4$ and $R_5$ may also form heterocyclic rings.

Y is N or O.

The vinylogous amides useful in the present invention can be prepared by dissolving equimolar amounts of a suitable amine and a suitable β-dicarbonyl in a 2 to 20 fold excess of methanol, ethanol, propanol, toluene or water. They may also be prepared in the absence of a solvent, if desired. The resultant mixture is stirred at 50° C. for about two hours to yield the desired vinylogous amide, although in the case of secondary amines some additional heating may be required.

The vinylogous amides described above include all cis-trans positional isomers thereof. Dimers and low polymers of the vinylogous amides can be prepared in a similar manner and are useful in the present invention.

Specific examples of vinylogous amides which are useful in the present invention include:

A. $CH_3-\overset{O}{\overset{\|}{C}}-CH=\underset{CH_3}{\overset{}{C}}-NH-C_8H_{17}$ 4-octylamino-3-pentene-2-one B. $CH_3-\overset{O}{\overset{\|}{C}}-CH=\underset{CH_3}{\overset{}{C}}-NH-C_{12}H_{25}$ 4-dodecylamino-3-pentene-2-one

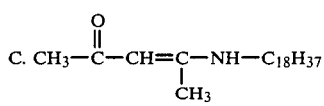

C. CH₃—C(=O)—CH=C(CH₃)—NH—C₁₈H₃₇

4-octadecylamino-3-pentene-2-one

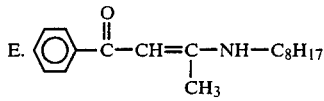

E. Ph—C(=O)—CH=C(CH₃)—NH—C₈H₁₇

3-octylamino-1-phenyl-2-butene-1-one

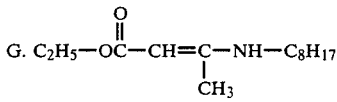

G. C₂H₅—OC(=O)—CH=C(CH₃)—NH—C₈H₁₇ ethyl 3-octylamino-2-butenoate

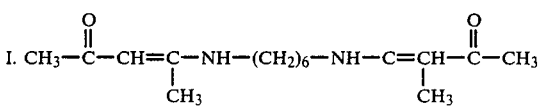

I. CH₃—C(=O)—CH=C(CH₃)—NH—(CH₂)₆—NH—C(CH₃)=CH—C(=O)—CH₃

4-[6-(4'-amino-3'-pentene-2'-one)-hexylamino]-3-pentene-2-one

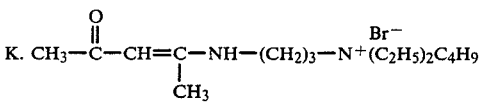

K. CH₃—C(=O)—CH=C(CH₃)—NH—(CH₂)₃—N⁺(C₂H₅)₂C₄H₉  Br⁻

4-(3-butyldiethylammonium)-propylamino-3-pentene-2-one bromide

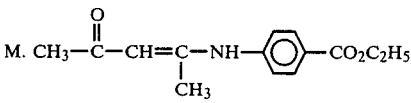

M. CH₃—C(=O)—CH=C(CH₃)—NH—C₆H₄—CO₂C₂H₅

4-(p-carboxyethylphenyl)-amino-3-pentene-2-one

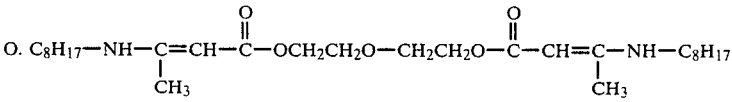

O. C₈H₁₇—NH—C(CH₃)=CH—C(=O)—OCH₂CH₂O—CH₂CH₂O—C(=O)—CH=C(CH₃)—NH—C₈H₁₇ bis(3-octylamino-2-butenoyl)-B,B'—dioxyethylether

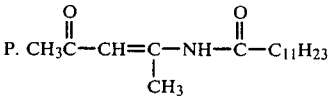

P. CH₃C(=O)—CH=C(CH₃)—NH—C(=O)—C₁₁H₂₃

4-dodecanoylamino-3-pentene-2-one

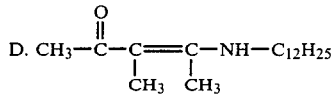

D. CH₃—C(=O)—C(CH₃)=C(CH₃)—NH—C₁₂H₂₅

4-dodecylamino-3-methyl-3-pentene-2-one

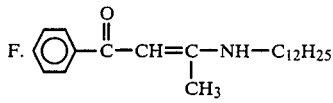

F. Ph—C(=O)—CH=C(CH₃)—NH—C₁₂H₂₅

3-dodecylamino-1-phenyl-2-butene-1-one

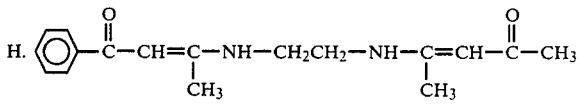

H. Ph—C(=O)—CH=C(CH₃)—NH—CH₂CH₂—NH—C(CH₃)=CH—C(=O)—CH₃

3-[2-(4'-amino-3'-pentene-2'-one)-ethylamino]-1-phenyl-2-butene-1-one

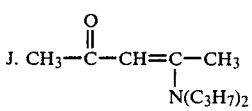

J. CH₃—C(=O)—CH=C(CH₃)—N(C₃H₇)₂·

4-dipropylamino-3-pentene-2-one

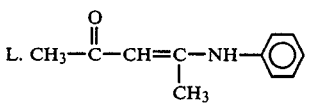

L. CH₃—C(=O)—CH=C(CH₃)—NH—Ph 4-phenylamino-3-pentene-2-one

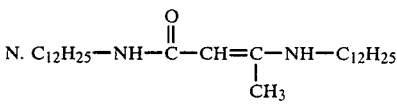

N. C₁₂H₂₅—NH—C(=O)—CH=C(CH₃)—NH—C₁₂H₂₅ dodecyl 3-dodecylamino-2-butenamide

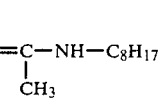

Q. Ph—C(=O)—CH=C(CH₃)—NH—C₁₈H₂₇

3-octadecylamino-1-phenyl-2-butene-1-one

The vinylogous amides useful in the formulations of the present invention exhibit light absorbance maxima in either the UV-A or UV-B regions and thus depending on the choice of specific vinylogous amides one can formulate compositions which are effective sunscreens in either of these regions or by selecting a mixture of said vinylogous amides in both regions of the spectrum. It is also possible and may sometimes be desirable to combine the vinylogous amide sunscreen agents with conventional sunscreen agents to form effective sunscreen compositions.

The sunscreen compositions of the present invention contain the sunscreen agent or combination of sunscreen agents and a pharmaceutically extending medium such as a carrier or vehicle which adapts said agents for application to the skin. These compositions can be in either solid, liquid or aerosol form. The sunscreen agents of the present invention can also be incorporated into various cosmetic and personal care products such as hand and body lotions, oils, ointments, lip balm products, facial cosmetics and the like.

The amount of sunscreen agent present in the sunscreen compositions or the cosmetic and personal care products may vary greatly but is preferable in a range of about 1 to 20% by weight of the total composition. One or more sunscreen agents may be utilized with the combined concentration of said agents preferably in the range of 1 to 20% by weight of the composition.

Greater amounts of these agents may be incorporated into various products limited only by processing and economic considerations.

Specific embodiments of the present invention are illustrated by the following examples. It will be understood, however, that the invention is not confined to the specific limitations set forth in the individual examples, but rather to the scope of the appended claims.

EXAMPLE I

Preparation of Compound (A)

100.12 g (1 mole) of pentane-2,4-dione and 129.25 g (1 mole) of n-octylamine are mixed with vigorous stirring and exotherm to 50° C. over a ten minute period. After one hour the reaction product cools and yields 211 g of a compound of the formula

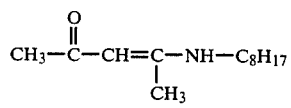

EXAMPLE II

Preparation of Compound (G)

130.41 g (1 mole) of ethyl acetoacetate and 129.25 g (1 mole) of n-octylamine are mixed in 300 ml of 95% ethanol. The solution is mixed under reflux for a period of four hours. Removal of the solvent under reduced pressure yields 241 g of a compound of the formula

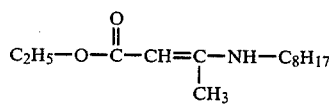

EXAMPLE III

Preparation of Compound (F)

162.19 g (1 mole) of benzoylacetone and 185.36 g (1 mole) of dodecylamine are dissolved in 1000 ml. of methanol. The solution is heated at about 60° C. for 5 hours. Removal of the solvent under reduced pressure yields 329 g of a compound of the formula

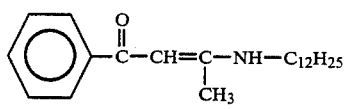

EXAMPLE IV

A sunscreen formulation is prepared according to the following procedure. In a suitable beaker, with vigorous agitation, 1.50 g of Carbopol 941 thickening agent, 0.25 g disodium ethylene diamine tetraacetate (disodium EDTA) preservative and chelating agent, 1.00 g Methocel K100LV stabilizer and 0.65 g Kathon CG preservative are added to 354.1 g of deionized water and heated to 70° C. 15.00 g of a 7.5% solution of ammonium hydroxide are added and mixing continues for 5 minutes. In a second beaker, 5.00 g stearyl alcohol emollient, 10.00 g Emerest 2400 emollient, 10.00 g mineral oil emollient, 2.50 g dimethicone emollient, 25.00 g Finsolv TN emollient and 15.00 g isostearic acid emulsifier are heated to 70° C. In a third beaker, 25.00 g of Compound A, 15.00 g of Compound E and 20.00 g of Compound G are premelted at 70° C. and then added to the contents in the second beaker and mixed for five minutes at 70° C. The contents of the second beaker are then added to the first beaker and the resulting emulsion is cooled to 50° C., homogenized, and cooled to room temperature.

The resulting composition is an emulsion which is an opaque, free flowing lotion having a pH of about 8.6 and a viscosity of about 20,000 centistokes.

The resulting composition has the following formulation:

| Ingredient | % by wt. |
| --- | --- |
| Carbopol 941 (B. F. Goodrich's tradename for carboxy vinyl polymer) | 0.30 |
| disodium EDTA | 0.05 |
| Methocel K100LV (Dow Chemical's tradename for hydroxypropyl methylcellulose) | 0.20 |
| Kathon CG (Rohm & Haas' tradename for methyl-and methylchloro-isothiazolinones) | 0.13 |
| ammonium hydroxide (7.5%) | 3.00 |
| stearyl alcohol | 1.00 |
| Emerest 2400 (Emery Industries tradename for glyceryl stearate) | 2.00 |
| mineral oil | 2.00 |
| isostearic acid | 3.00 |
| dimethicone, 50 cs. | 0.50 |
| Finsolv TN (Finetex's tradename for $C_{12}$-$C_{15}$ alcohol benzoates) | 5.00 |
| Compound A | 5.00 |
| Compound E | 3.00 |
| Compound G | 4.00 |
| deionized water | balance to 100.00 |

EXAMPLE V

A sunscreen composition is prepared in accordance with the procedure of Example IV and consists of the following ingredients:

| Ingredient | % by wt. |
| --- | --- |
| Carbopol 934 (B. F. Goodrich's tradename for carboxy vinyl polymer) | 0.30 |
| disodium EDTA | 0.05 |
| Methocel J40MS (Dow Chemical's tradename for hydroxypropyl methylcellulose) | 0.50 |
| Kathon CG | 0.13 |
| ammonium hydroxide (7.5%) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| BHT (trade usage for butylated hydroxytoluene) | 0.05 |
| Compound A | 5.00 |
| Compound F | 3.00 |
| Compound G | 4.00 |
| deionized water | balance to 100.00 |

The resulting composition is a white, opaque lotion having a pH of 8.56 and a viscosity of 20,000 centistokes.

EXAMPLE VI

A sunscreen composition is prepared in accordance with the procedure of Example IV and consists of the following ingredients:

| Ingredient | % by wt. |
| --- | --- |
| Carbopol 934 | 0.30 |
| disodium EDTA | 0.05 |
| Methocel J40MS | 0.50 |
| Kathon CG | 0.13 |
| ammonium hydroxide (7.5% sol'n) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| BHT | 0.05 |
| Compound A | 8.00 |
| Compound F | 3.00 |
| Compound G | 4.00 |
| deionized water | balance to 100.00 |

The resulting composition is a white, opaque lotion.

EXAMPLE VII

A sunscreen formulation is prepared in accordance with the procedure of Example IV and consists of the following ingredients:

| Ingredient | % by wt. |
| --- | --- |
| Carbopol 941 | 0.30 |
| disodium EDTA | 0.05 |
| Methocel K100LV | 0.20 |
| Kathon CG | 0.13 |
| ammonium hydroxide (7.5%) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| Padimate O (trade designation for 2-ethylhexyl-p-dimethylaminobenzoate) | 5.00 |
| Compound E | 3.00 |
| Compound G | 4.00 |
| deionized water | balance to 100.00 |

The resulting composition is a white, free-flowing lotion.

EXAMPLE VIII

A sunscreen formulation is prepared according to the procedure of Example IV and consists of the following ingredients:

| Ingredient | % by wt. |
| --- | --- |
| Carbopol 941 | 0.30 |
| disodium EDTA | 0.05 |
| Methocel K100LV | 0.20 |
| Kathon CG | 0.13 |
| ammonium hydroxide (7.5%) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| Compound A | 5.00 |
| deionized water | balance to 100.00 |

The resulting composition is a white, free-flowing lotion.

EXAMPLE IX

A hand and body lotion composition is prepared as follows:

In a suitable beaker with vigorous agitation, 3.0 g of Carbopol 934 and 40 g propylene glycol are added to 788.7 g deionized water and heated to 70° C. In a second beaker, 10 g isopropylpalmitate, 10.0 g dimethicone (50 cs), 12.5 g oleic acid, 10.0 g stearoxymethylsilane, 8.0 g sorbitan stearate, 5.0 g cetyl alcohol, 5.0 g stearyl alcohol, 5.0 g synthetic beeswax, 12.5 g glyceryl monostearate, 12.5 g stearic acid, 12.0 g polysorbate 61, 15.0 g myristyl myristate, 2.0 g BHT and 3.0 g benzyl alcohol are melted. The contents of the second beaker are added to the contents of the first beaker and to the resultant mixture are added 0.5 g butylparaben, 1.0 g propylparaben and 1.5 g methylparaben followed by the addition of 2.6 g of a 50% solution of sodium hydroxide, 20.0 g of Compound A and 20.0 g of Compound E. The resulting emulsion is homogenized and cooled to 45° C. at which point 2.0 g of fragrance are added followed by cooling to room temperature resulting in a thick, white lotion.

The resulting composition has the following formulation:

| Ingredients | % by wt. |
| --- | --- |
| Carbopol 934 | 0.30 |
| propylene glycol | 4.00 |
| isopropyl palmitate | 1.00 |
| dimethicone, 50 cs. | 1.00 |
| oleic acid | 1.25 |
| stearoxymethylsilane | 1.00 |
| sorbitan stearate | 0.80 |
| cetyl alcohol | 0.50 |
| stearyl alcohol | 0.50 |
| synthetic beeswax | 0.50 |
| glyceryl monostearate | 1.25 |
| stearic acid | 1.25 |
| polysorbate 61 | 1.20 |
| myristyl myristate | 1.50 |
| butylparaben | 0.05 |
| propylparaben | 0.10 |
| methylparaben | 0.15 |
| BHT | 0.02 |
| sodium hydroxide (50%) | 0.26 |
| benzyl alcohol | 0.30 |
| fragrance | 0.20 |
| Compound A | 2.00 |
| Compound E | 2.00 |
| deionized water | balance to 100.00 |

EXAMPLE X

A lotion formulation is prepared according to the procedure of Example IX and consists of the following ingredients:

| Ingredients | % by wt. |
| --- | --- |
| Carbopol 934 | 0.30 |
| propylene glycol | 4.00 |
| isopropyl palmitate | 1.00 |
| dimethicone, 50 cs. | 1.00 |
| oleic acid | 1.25 |
| stearoxymethylsilane | 1.00 |
| sorbitan stearate | 0.80 |
| cetyl alcohol | 0.50 |
| stearyl alcohol | 0.50 |
| synthetic beeswax | 0.50 |
| glyceryl monostearate | 1.25 |
| stearic acid | 1.25 |
| polysorbate 61 | 1.20 |
| myristyl myristate | 1.50 |

-continued

| Ingredients | % by wt. |
|---|---|
| butylparaben | 0.05 |
| propylparaben | 0.10 |
| methylparaben | 0.15 |
| BHT | 0.02 |
| sodium hydroxide (50%) | 0.26 |
| benzyl alcohol | 0.30 |
| fragrance | 0.20 |
| Padimate O | 4.00 |
| Compound G | 3.00 |
| deionized water | balance to 100.00 |

The resulting composition is a thick, white lotion.

EXAMPLE XI

A lotion formulation is prepared according to the procedure of Example IX and consists of the following ingredients:

| Ingredients | % by wt. |
|---|---|
| Carbopol 934 | 0.30 |
| propylene glycol | 4.00 |
| isopropyl palmitate | 1.00 |
| dimethicone, 50 cs. | 1.00 |
| oleic acid | 1.25 |
| stearoxymethylsilane | 1.00 |
| sorbitan stearate | 0.80 |
| cetyl alcohol | 0.50 |
| stearyl alcohol | 0.50 |
| synthetic beeswax | 0.50 |
| glyceryl monostearate | 1.25 |
| stearic acid | 1.25 |
| polysorbate 61 | 1.20 |
| myristyl myristate | 1.50 |
| butylparaben | 0.05 |
| propylparaben | 0.10 |
| methylparaben | 0.15 |
| BHT | 0.02 |
| sodium hydroxide (50%) | 0.26 |
| benzyl alcohol | 0.30 |
| fragrance | 0.20 |
| octyl salicylate | 2.00 |
| Compound F | 1.00 |
| deionized water | balance to 100.00 |

The resulting composition is a thick, white lotion.

EXAMPLE XII

A lotion formulation is prepared according to the procedure of Example IX and consists of the following ingredients:

| Ingredients | % by wt. |
|---|---|
| Carbopol 934 | 0.30 |
| propylene glycol | 4.00 |
| isopropyl palmitate | 1.00 |
| dimethicone, 50 cs. | 1.00 |
| oleic acid | 1.25 |
| stearoxymethylsilane | 1.00 |
| sorbitan stearate | 0.80 |
| cetyl alcohol | 0.50 |
| stearyl alcohol | 0.50 |
| synthetic beeswax | 0.50 |
| glyceryl monostearate | 1.25 |
| stearic acid | 1.25 |
| polysorbate 61 | 1.20 |
| butylparaben | 0.05 |
| propylparaben | 0.10 |
| methylparaben | 0.15 |
| BHT | 0.02 |
| sodium hydroxide (50%) | 0.26 |
| benzyl alcohol | 0.30 |
| fragrance | 0.20 |
| Compound G | 3.00 |
| Compound Q | 5.00 |
| Compound B | 4.00 |
| deionized water | balance to 100.00 |

The resulting composition is a thick, white lotion.

EXAMPLE XIII

A hand cream composition is prepared according to the following procedure. In a suitable beaker 367.4 g mineral oil, 55.0 g lanolin, 80.0 g white wax, 45.7 g paraffin, 70.0 g synthetic beeswax, 10.0 g glyceryl monostearate and 68.5 g white ceresine wax are melted and kept at a temperature of 70° C. In a second beaker 241.8 g of deionized water, 9.0 g powdered borax and 1.0 g propylparaben are heated to 70° C. and the contents of the first beaker are added to the second beaker and 30 g of Compound A and 20.0 g of Compound Q are added thereto. The mixture is cooled to 55° C. and 1.6 g of fragrance are added and the cooling continued to 45° C. and the resulting composition filled in a suitable container and cooled to room temperature.

The resulting composition has the following formulation:

| Ingredients | % by wt. |
|---|---|
| mineral oil | 36.74 |
| lanolin, anhydrous cosmetic grade | 5.50 |
| white wax, USP | 8.00 |
| paraffin | 4.57 |
| synthetic beeswax | 7.00 |
| glyceral monostearate | 1.00 |
| white ceresine wax | 6.85 |
| powdered borax | 0.90 |
| fragrance | 0.16 |
| propylparaben | 0.10 |
| Compound A | 3.00 |
| Compound Q | 2.00 |
| deionized water | balance to 100.00 |

EXAMPLE XIV

A hand cream formulation is prepared according to the procedure of Example XIII and consists of the following ingredients:

| Ingredients | % by wt. |
|---|---|
| mineral oil | 36.74 |
| lanolin, anhydrous cosmetic grade | 5.50 |
| white wax, USP | 8.00 |
| paraffin | 4.57 |
| synthetic beeswax | 7.00 |
| glyceryl monostearate | 1.00 |
| white ceresine wax | 6.85 |
| powdered borax | 0.90 |
| fragrance | 0.16 |
| propylparaben | 0.10 |
| Compound G | 3.00 |
| Compound C | 2.00 |
| Compound E | 2.00 |
| deionized water | balance to 100.00 |

EXAMPLE XV

A hand cream formulation is prepared according to the procedure of Example XIII and consists of the following ingredients:

| Ingredients | % by wt. |
| --- | --- |
| mineral oil | 36.74 |
| lanolin, anhydrous cosmetic grade | 5.50 |
| white wax, USP | 8.00 |
| paraffin | 4.57 |
| synthetic beeswax | 7.00 |
| glyceryl monostearate | 1.00 |
| white ceresine wax | 6.85 |
| powdered borax | 0.90 |
| fragrance | 0.16 |
| propylparaben | 0.10 |
| octyl salicylate | 3.00 |
| Compound E | 4.00 |
| deionized water | balance to 100.00 |

EXAMPLE XVI

A hand cream formulation is prepared according to the procedure of Example XIII and consists of the following ingredients:

| Ingredients | % by wt. |
| --- | --- |
| mineral oil | 36.74 |
| lanolin, anhydrous cosmetic grade | 5.50 |
| white wax, USP | 8.00 |
| paraffin | 4.57 |
| synthetic beeswax | 7.00 |
| glyceryl monostearate | 1.00 |
| white ceresine wax | 6.85 |
| powdered borax | 0.90 |
| fragrance | 0.16 |
| propylparaben | 0.10 |
| Compound E | 1.00 |
| Compound B | 1.00 |
| deionized water | balance to 100.00 |

EXAMPLE XVII

A dry skin composition is prepared in accordance with the following procedure. In a suitable beaker 410.0 g petrolatum, 30.0 g polyethylene and 20.0 g silicon dioxide are melted at 80° C. and homogenized. To this mixture, 338.0 g cyclomethicone, 100.0 g dimethicone, 10.0 g mineral oil, 1.0 g propylparaben, 1.0 g sorbic acid, 50.0 g Compound A and 40.0 g Compound F are added and the resultant mixture is cooled to 35° C.

The resulting composition has the following formulation:

| Ingredients | % by wt. |
| --- | --- |
| petrolatum, white USP | 41.0 |
| polyethylene | 3.0 |
| silicon dioxide | 2.0 |
| cyclomethicone | 33.8 |
| dimethicone, 50 cs. | 10.0 |
| mineral oil | 1.0 |
| propylparaben | 0.1 |
| sorbic acid | 0.1 |
| Compound A | 5.0 |
| Compound F | 4.0 |
| | 100.0 |

EXAMPLE XVIII

A dry skin formulation is prepared according to the procedure of Example XVIII and consists of the following ingredients:

| Ingredients | % by wt. |
| --- | --- |
| petrolatum, white USP | 42.0 |
| polyethylene | 3.0 |
| silicon dioxide | 2.0 |
| cyclomethicone | 33.8 |
| dimethicone, 50 cs. | 10.0 |
| mineral oil | 1.0 |
| propylparaben | 0.1 |
| sorbic acid | 0.1 |
| Compound G | 5.0 |
| Compound C | 4.0 |
| Compound Q | 3.0 |
| | 100.0 |

EXAMPLE XIX

A dry skin formulation is prepared according to the procedure of Example XVII and consists of the following ingredients:

| Ingredients | % by wt. |
| --- | --- |
| petrolatum, white USP | 45.0 |
| polyethylene | 3.0 |
| silicon dioxide | 2.0 |
| cyclomethicone | 33.8 |
| dimethicone, 50 cs. | 10.0 |
| mineral oil, J & J Special | 1.0 |
| propylparaben | 0.1 |
| sorbic acid | 0.1 |
| Padimate O | 3.0 |
| Compound E | 2.0 |
| | 100.0 |

EXAMPLE XX

A dry skin formulation is prepared according to the procedure of Example XVII and consists of the following ingredients:

| Ingredients | % by wt. |
| --- | --- |
| petrolatum, white USP | 45.0 |
| polyethylene | 3.0 |
| silicon dioxide | 2.0 |
| cyclomethicone | 33.8 |
| dimethicone, 50 cs. | 10.0 |
| mineral oil | 1.0 |
| propylparaben | 0.1 |
| sorbic acid | 0.1 |
| oxybenzone | 2.0 |
| Compound B | 3.0 |
| | 100.0 |

EXAMPLE XXI

A lip balm composition is prepared according to the following procedure. In a suitable beaker 72.0 g petrolatum, 8.0 g Syncrowax HRC, 8.0 g Syncrowax ERL-C, 8.0 g Syncrowax HGL-C, 2.0 g Compound A and 2.0 g oxybenzone are added. The mixture is melted and cast into sticks at a temperature of 60° C.

The resulting composition has the following formulation:

| Ingredients | % by wt. |
| --- | --- |
| petrolatum, white USP | 72.0 |
| Syncrowax HRC (Croda's tradename for glyceryl tribehenate) | 8.0 |
| Syncrowax ERL-C (Croda's tradename for | 8.0 |

| Ingredients | % by wt. |
| --- | --- |
| C$_{18}$-C$_{36}$ wax fatty acid-ethylene glycol ester) Syncrowax HGL-C (Croda's tradename for C$_{18}$-C$_{36}$ wax fatty acid triglyceride) | 8.0 |
| Compound A | 2.0 |
| oxybenzone | 2.0 |
| | 100.0 |

EXAMPLE XXII

A lip balm composition is prepared according to the procedure of Example XXI and consists of the following ingredients:

| Ingredients | % by wt. |
| --- | --- |
| petrolatum, white USP | 66.0 |
| Syncrowax HRC | 8.0 |
| Syncrowax ERL-C | 8.0 |
| Syncrowax HGL-C | 8.0 |
| Compound G | 3.0 |
| Compound C | 4.0 |
| Compound F | 3.0 |
| | 100.0 |

EXAMPLE XXIII

A lip balm composition is prepared according to the procedure of Example XXI and consists of the following ingredients:

| Ingredients | % by wt. |
| --- | --- |
| petrolatum, white USP | 67.0 |
| Syncrowax HRC | 8.0 |
| Syncrowax ERL-C | 8.0 |
| Syncrowax HGL-C | 8.0 |
| Compound G | 2.0 |
| Padimate O | 4.0 |
| Compound Q | 3.0 |
| | 100.0 |

EXAMPLE XXIV

A lip balm composition is prepared according to the procedure of Example XXI and consists of the following ingredients:

| Ingredients | % by wt. |
| --- | --- |
| petrolatum, white USP | 74.0 |
| Syncrowax HRC | 8.0 |
| Syncrowax ERL-C | 8.0 |
| Syncrowax HGL-C | 8.0 |
| octyl salicylate | 1.0 |
| Compound E | 1.0 |
| | 100.0 |

EXAMPLE XXV

A mineral oil composition is prepared according to the following procedure. In a suitable beaker 97.0 g of mineral oil, 1.0 g Compound G, 1.0 g Compound C and 1.0 g oxybenzone are melted until uniform and cooled to room temperature.

The resulting composition has the following formulation:

| Ingredients | % by wt. |
| --- | --- |
| mineral oil | 97.0 |
| Compound G | 1.0 |
| Compound C | 1.0 |
| oxybenzone | 1.0 |
| | 100.0 |

EXAMPLE XXVI

A mineral oil composition is prepared according to the procedure of Example XXV and consists of the following ingredients:

| Ingredients | % by wt. |
| --- | --- |
| mineral oil | 93.0 |
| Padimate O | 3.0 |
| Compound F | 4.0 |
| | 100.0 |

EXAMPLE XXVII

A mineral oil composition is prepared according to the procedure of Example XXV and consists of the following ingredients:

| Ingredients | % by wt. |
| --- | --- |
| mineral oil | 93.0 |
| Compound G | 2.0 |
| octyl salicylate | 3.0 |
| Compound Q | 2.0 |
| | 100.0 |

EXAMPLE XXVIII

A mineral oil composition is prepared according to the procedure of Example XXV and consists of the following ingredients:

| Ingredients | % by wt. |
| --- | --- |
| mineral oil | 98.0 |
| Compound E | 1.0 |
| Compound B | 1.0 |
| | 100.0 |

What is claimed is:

1. A sunscreen composition comprising an extending medium and from about 1 to 20% by weight of the total composition of at least one vinylogous amide compound of the formula

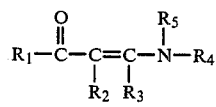

wherein
R$_1$ is selected from alkyl, cycloalkyl, alkenyl, cycloalkenyl, aryl, substituted aryl or alkaryl of from 1 to 18 carbon atoms;
R$_2$ and R$_3$ may be the same or different and are selected from hydrogen, alkyl, alkenyl, cycloalkyl or cycloalkenyl of from 1 to 18 carbon atoms;
R$_4$ and R$_5$ may be the same or different and are selected from hydrogen, alkyl, alkenyl, aryl and substituted aryl, alkaryl, cycloalkyl or cycloalkenyl of from 1 to 18 carbon atoms.

2. The composition of claim 1 wherein the vinylogous amide is of the formula

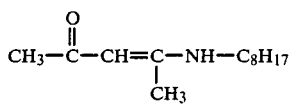

3. The composition of claim 1 wherein the vinylogous amide is of the formula

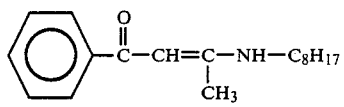

4. The composition of claim 1 wherein the vinylogous amide is of the formula

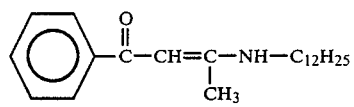

5. The composition of claim 1 containing at least one vinylogous amide and in addition oxybenzone.

6. The composition of claim 1 containing at least one vinylogous amide and in addition 2-ethylhexyl-p-dimethylaminobenzoate.

7. A method of protecting human skin from the erythmic effects of ultraviolet radiation which comprises applying to the skin a sunscreen composition containing an extending medium and from about 1 to 20% by weight of the total composition of at least one compound of the formula

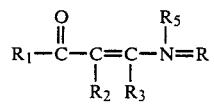

wherein
$R_1$ is selected from alkyl, cycloalkyl, alkenyl, cycloalkenyl, aryl, substituted aryl or alkaryl of from 1 to 18 carbon atoms;
$R_2$ and $R_3$ may be the same or different and are selected from hydrogen, alkyl, alkenyl, cycloalkyl or cycloalkenyl of from 1 to 18 carbon atoms;
$R_4$ and $R_5$ may be the same or different and are selected from hydrogen, alkyl, alkenyl, aryl and substituted aryl, alkaryl, cycloalkyl or cycloalkenyl of from 1 to 18 carbon atoms.

* * * * *